US008313330B2

(12) United States Patent
Maspoli et al.

(10) Patent No.: US 8,313,330 B2
(45) Date of Patent: Nov. 20, 2012

(54) SYSTEMS AND METHODS FOR MEDICAL TOOL AUTO-CAPTURE

(75) Inventors: Peter Maspoli, Washington, DC (US); John Michael Brown, Washington, DC (US); Robert F. Cohen, Kensington, MD (US)

(73) Assignee: Immersion Corporation, San Jose, CA (US)

( * ) Notice: Subject to any disclaimer, the term of this patent is extended or adjusted under 35 U.S.C. 154(b) by 1404 days.

(21) Appl. No.: 11/941,401

(22) Filed: Nov. 16, 2007

(65) Prior Publication Data

US 2008/0126041 A1 May 29, 2008

Related U.S. Application Data

(60) Provisional application No. 60/859,924, filed on Nov. 16, 2006.

(51) Int. Cl.
*G09B 23/28* (2006.01)
(52) U.S. Cl. ..................................................... 434/262
(58) Field of Classification Search .................. 434/262, 434/272; 483/7–9; 600/118; 606/1, 42; 700/254, 248, 249
See application file for complete search history.

(56) References Cited

U.S. PATENT DOCUMENTS

| | | | | |
|---|---|---|---|---|
| 4,922,591 A * | 5/1990 | Campbell | ......................... | 483/1 |
| 7,008,362 B2 * | 3/2006 | Fitzgibbon | ......................... | 483/9 |
| 7,217,229 B2 * | 5/2007 | Hagihara et al. | .................. | 483/7 |
| 7,437,210 B1 * | 10/2008 | Shigefuji et al. | .............. | 700/160 |
| 7,485,082 B2 * | 2/2009 | Yoshida | ............................. | 483/7 |
| 7,720,570 B2 * | 5/2010 | Close et al. | ..................... | 700/245 |
| 8,005,571 B2 * | 8/2011 | Sutherland et al. | ............ | 700/248 |
| 2002/0052272 A1 * | 5/2002 | Izumi | .................................... | 483/7 |
| 2002/0072736 A1 * | 6/2002 | Tierney et al. | ..................... | 606/1 |
| 2003/0216715 A1 * | 11/2003 | Moll et al. | ......................... | 606/1 |
| 2004/0243147 A1 * | 12/2004 | Lipow | ........................... | 606/130 |
| 2006/0161136 A1 * | 7/2006 | Anderson et al. | .................. | 606/1 |
| 2007/0137372 A1 * | 6/2007 | Devengenzo et al. | ...... | 74/490.01 |
| 2007/0299427 A1 * | 12/2007 | Yeung et al. | ....................... | 606/1 |
| 2009/0326324 A1 * | 12/2009 | Munoz Martinez et al. | . | 600/118 |
| 2010/0204713 A1 * | 8/2010 | Ruiz Morales | ............... | 606/130 |

FOREIGN PATENT DOCUMENTS

WO WO 99/39317 8/1999

* cited by examiner

*Primary Examiner* — Kurt Fernstrom
(74) *Attorney, Agent, or Firm* — Kilpatrick, Townsend & Stockton LLP

(57) ABSTRACT

Systems and methods for medical tool auto-capture are described. One described system for simulation of a medical procedure comprises a first grasper comprising a first grasper proximal end and a first grasper distal end. The system further comprises a first sensor coupled to the first grasper distal end and configured to identify a first medical tool approaching the first sensor, wherein the first grasper is configured to automatically grasp the first medical tool upon the first sensor identifying the first medical tool. The system also comprises an actuator to provide a haptic effect to a user.

25 Claims, 15 Drawing Sheets

SYSTEMS AND METHODS FOR MEDICAL TOOL AUTO-CAPTURE

CROSS-REFERENCE TO RELATED APPLICATION

This application claims priority to U.S. Provisional Patent Application No. 60/859,924 filed Nov. 16, 2006. entitled "Systems and Methods for Medical Device Auto-Capture." the entirety of which is hereby incorporated by reference.

FIELD OF THE INVENTION

Embodiments of the present invention relate generally to systems and methods for simulation of a medical procedure. More specifically, embodiments of the present invention relate to systems and methods for medical tool auto-capture.

BACKGROUND

Today, medical simulation systems exist to train physicians inexperienced in specific medical procedures or to sharpen the memory or senses of seasoned physicians. One category of medical procedures for simulation includes medical operations within blood vessels. In such operations, concentric medical tools, such as a catheter and guidewire, may be inserted into the blood vessel through a restricted opening into the blood vessel. Therefore, a medical simulation system has a user insert the tools into an opening and attempt to simulate the medical procedure as the user moves the tools in and out of the opening.

One problem with existing medical simulation systems is that conventional computer simulation systems may not provide an immersive feel. As a result, a doctor may need to interact with the simulation system in a way that may not occur while performing the procedure on a live subject. For example, a simulation system may require a doctor to enter settings for particular tools to be used, to change the view or perspective of the subject, or to physically interface the tool and the system before interaction by the system with the tool.

SUMMARY

Embodiments of the present invention provide systems and methods for medical tool auto-capture in simulation of a medical procedure. In one embodiment, one described system for simulation of a medical procedure comprises a first grasper comprising a first grasper proximal end and a first grasper distal end. The system further comprises a first sensor coupled to the first grasper distal end and configured to identify a first medical tool approaching the first sensor, wherein the first grasper is configured to automatically grasp the first medical tool upon the first sensor identifying the first medical tool. The system also comprises an actuator coupled to the first grasper configured to provide a haptic effect to a user.

This illustrative embodiment is mentioned not to limit or define the invention, but to provide examples to aid understanding thereof. Illustrative embodiments are discussed in the Detailed Description, and further description of the invention is provided there. Advantages offered by various embodiments of this invention may be further understood by examining this specification.

BRIEF DESCRIPTION OF THE DRAWINGS

These and other features, aspects, and advantages of the present invention are better understood when the following Detailed Description is read with reference to the accompanying drawings, described herein.

DETAILED DESCRIPTION OF PREFERRED EMBODIMENTS

Figure 1:
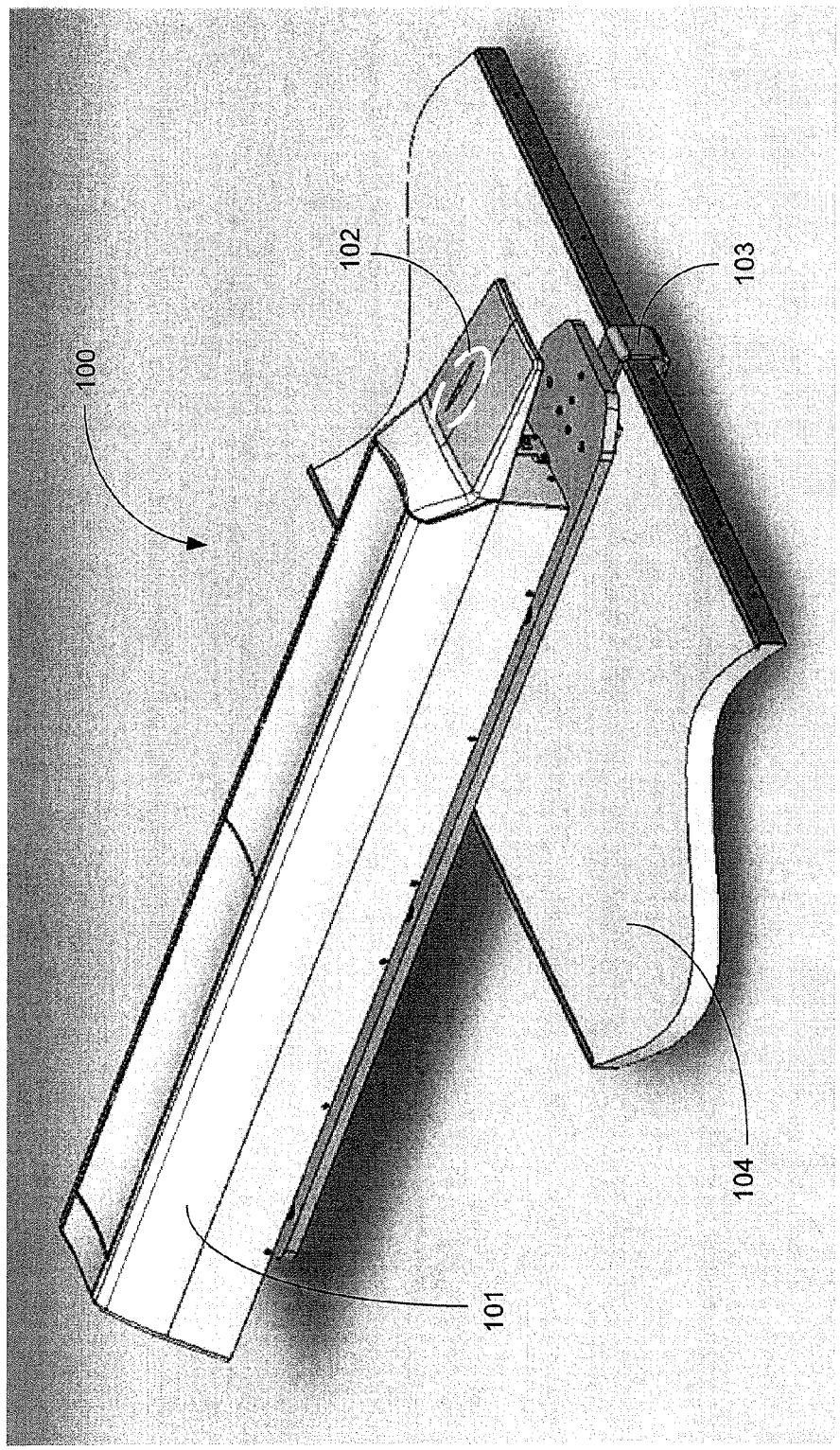
FIG. 1 is a perspective view of an illustrative system 100 for simulating a medical procedure in one embodiment of the present invention.

Embodiments of the present invention provide systems and methods for medical tool auto-capture. In one embodiment, the present invention relates to automatic capture of a medical tool during simulation. Throughout the description, for the purposes of explanation, numerous specific details are set forth in order to provide a thorough understanding of the present invention. It will be apparent, however, to one skilled in the art that the present invention may be practiced without some of these specific details. In other instances, well-known structures and devices are shown in block diagram form to avoid obscuring the underlying principles of the present invention.

Illustrative Medical Simulation System

One embodiment of the present invention comprises an integrated medical simulation environment for providing instruction to physicians for performing medical procedures in blood vessels, e.g., how to place an arterial stent in a patient's blood vessel. The integrated system includes a system to simulate a patient, wherein medical tools are inserted and feedback to/from the tools is generated/collected. The simulated patient may be placed on an operating table with a cloth draped over in order to simulate operation on an actual patient. The integrated system further includes a simulated scanning device and a display for visual simulation of the medical procedure. The integrated system also includes a medical tool auto-capture device inside the simulated patient and a variety of medical tools to insert into the simulated patient.

To simulate a medical procedure, the student or instructor selects a particular simulation to run. For example, the simulation may include the insertion of the stent in the aorta of the simulated patient. Selection of the simulation causes the scanning device, display, and medical tool auto-capture device to execute a simulation program based on a set of parameters that realistically simulate the particular procedure selected by the instructor.

The student selects a tool. For example, the student may select a canula and guidewire to insert into the simulated patient. As the student slides the canula into the medical tool auto-capture device, a first carriage within the device grasps the canula and produces a haptic effect to the student that simulates passage of the canula though a patient's artery. In this way, a student is able to learn the feel of inserting the medical tool in a real patient. The student may then slide the guidewire through the canula. The guidewire may be automatically captured by a second carriage within the auto-capture device, thereby simulating how a guidewire would feel as it progresses through a patient's arteries.

This illustrative example is given to introduce the reader to the general subject matter discussed herein. The invention is not limited to this example. The following sections describe various embodiments of systems and methods for medical tool auto-capture.

Illustrative System for Simulation of a Medical Procedure

FIG. 1 is a perspective view of an illustrative system 100 for, in one embodiment, simulating a medical procedure. In one embodiment, the system 100 comprises a casing 101 and an opening 102 for insertion and removal of medical tools. In one embodiment, medical tools for the system 100 may be actual medical tools used by a physician during surgery. In another embodiment, the medical tools may be proxy tools specific to the system 100 to act as an actual medical tool during simulation. Example medical tools that may be used in a medical procedure include, but are not limited to: a catheter, canula, guidewire, stent, stent delivery tool, balloon, electrical lead and embolic protection tool. The system 100 may further comprise a clasp 103 or other mechanism in order to secure the system 100 to a table top 104 (e.g., an operating table) or other surface. To simulate the system looking like an actual patient, a cloth may be draped over system 100 and/or the system molded into a human form.

In the following description, devices inside the system 100 are described as having a proximal end and a distal end. The proximal end of a device is the end closest to and approximately oriented toward the opening 102. The distal end of a device is the end farthest from and approximately oriented away from the opening 102.

Figure 2:
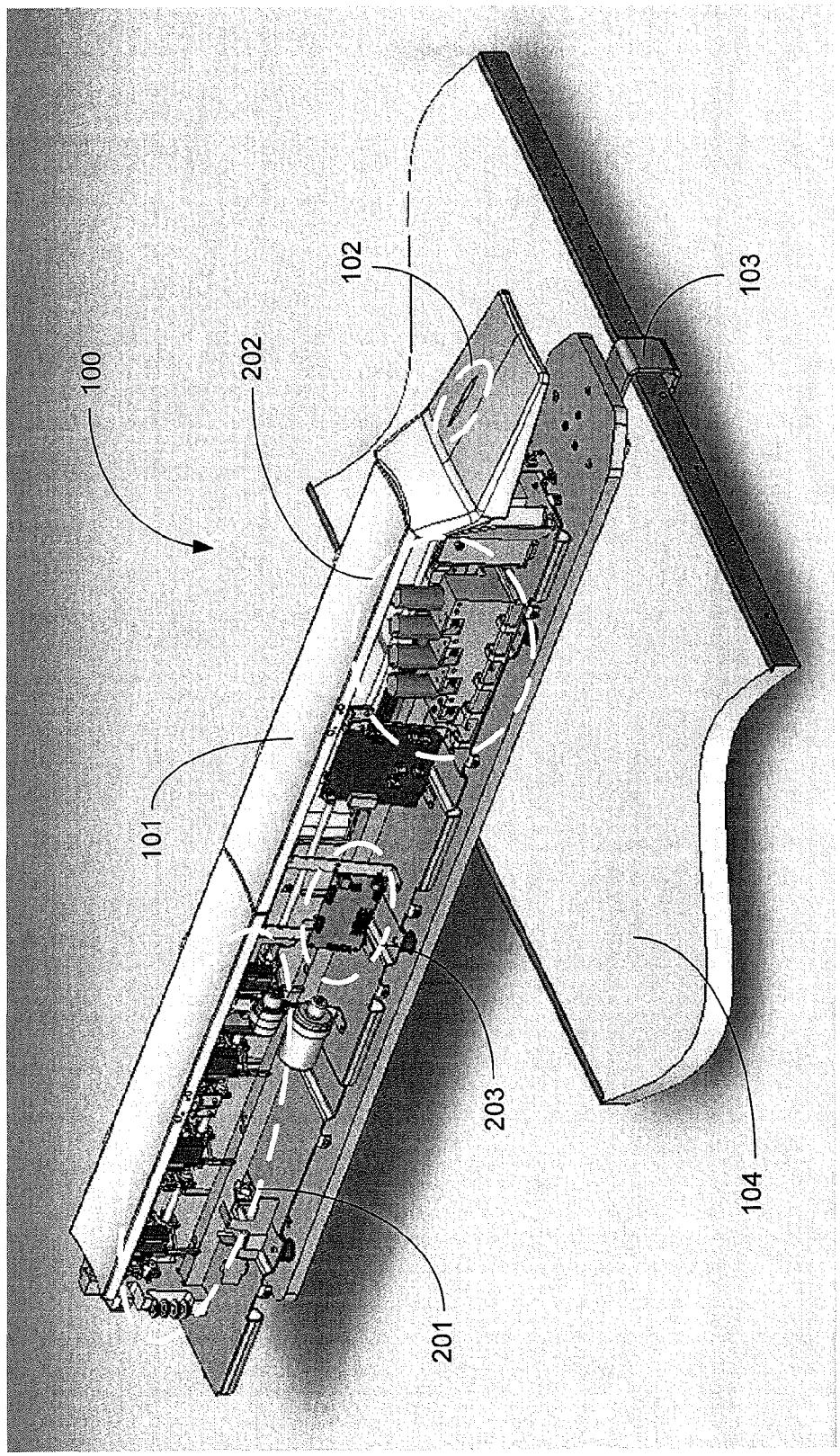
FIG. 2 is a perspective view of the illustrative system 100 in FIG. 1 where a portion of the cover is removed.

FIG. 2 is a perspective view of the system 100 in FIG. 1 where a portion of the cover 101 is removed. In the embodiment shown in FIG. 2, the system 100 includes a plurality of carriages 201 for identifying and grasping tools inserted through opening 102. The system 100 may further comprise a plurality of motors 202 or other actuators to provide haptic effects to the user through the tools grasped by the plurality of carriages 201. The system 100 may also comprise a control circuit 203 for controlling the physical processes of the carriages 201 and the motors 202.

Figure 3:
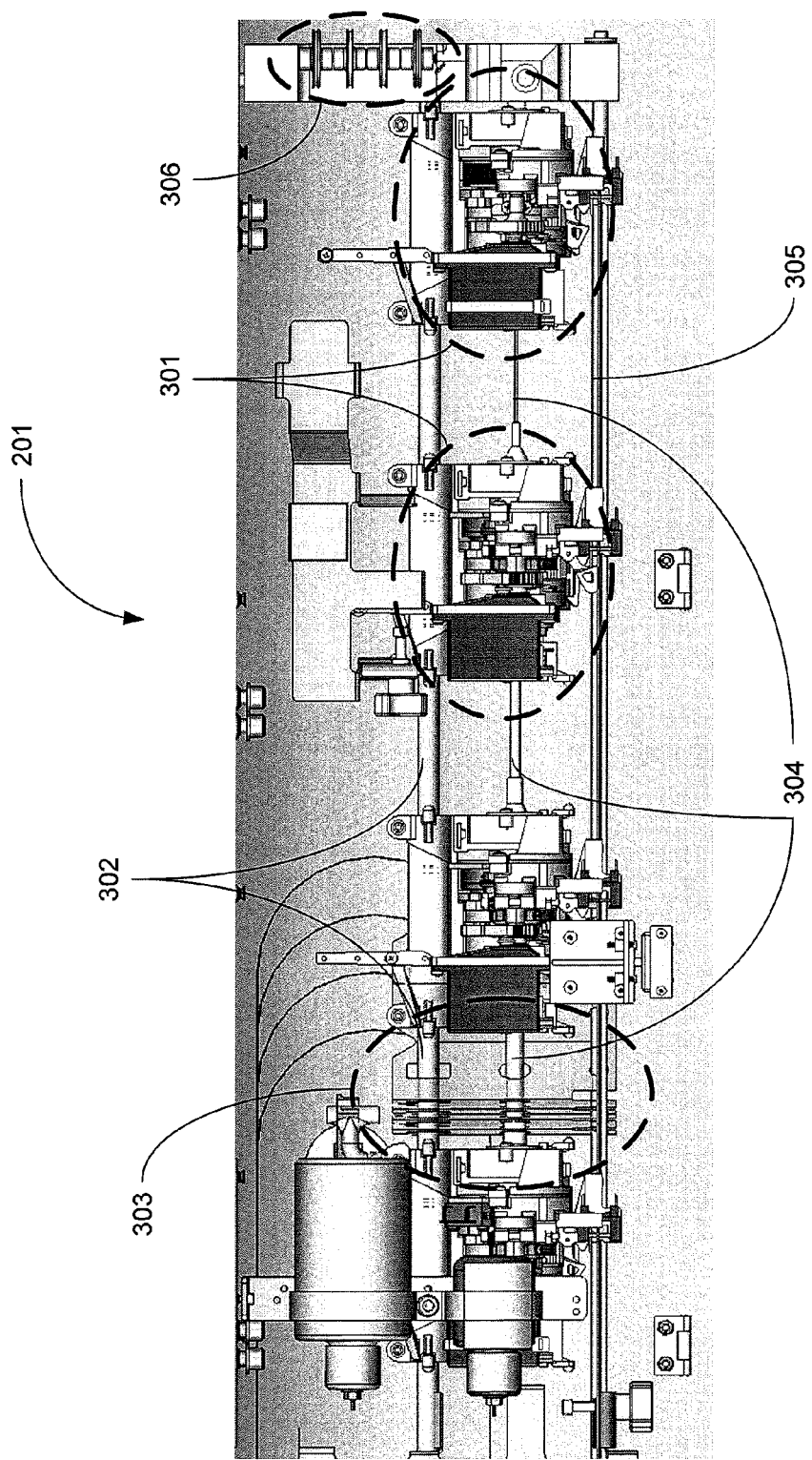
FIG. 3 shows a close up of the carriages of the system 100 in FIG. 2.

FIG. 3 shows a close-up view of the plurality of carriages 201 of the system 100 in FIG. 2. In one embodiment, the system 100 comprises carriages 301. In the embodiment shown in FIG. 3, the system 100 also comprises an assembly 302 for spacing the carriages 301 a minimum distance apart and a tool guide 303 for guiding tools 304 between carriages. In one embodiment, the minimum distance between carriages may be the distance between carriages so that they do not interfere with the operation of other neighboring carriages. In another embodiment, the minimum distance may be a predefined distance in order to allow a developer or user to know the relative position of the carriages in simulating a medical procedure or to determine the home position of each carriage. The system 100 also includes a rail 305 oriented along an axis for carriages to slide back and forth. While only a single rail is shown in FIG. 3, in other embodiments, a plurality of rails may be utilized.

The system 100 shown also comprises a plurality of pulleys or wheels 306. The plurality of wheels 306 each guide a wire coupled at both ends to a motor of the plurality of motors 202 (FIG. 2) and coupled at a position between the two ends to a carriage of the plurality of carriages 201. In one embodiment, the motor rolls the wire in one direction or the other (spinning a pulley of the plurality of pulleys 306) in order to move or to resist the movement of the attached carriage 301 along the rail(s) 305. In one embodiment, the motor provides resistance to moving the tool grasped by the attached carriage 301 (simulating resistance to the user) or assists the movement of the carriage 301 along the rail(s) 305 (in order to negate the momentum and resistance inherently associated with the carriage 301). In one embodiment, the motors may compensate for differing tensile flexibility of the wires attached to the motors and carriage in order to provide approximately uniform feedback. For example, shorter wires may stretch less. Therefore, less force may be applied by the motor in order to account for stretching of the wire. In one embodiment, the system may be configured to restrict the length of allowed displacement along the rail(s) 305 from a home position for each of the carriages 301. In one embodiment, the tool guide 303 may be a compoundly folded sheet that expands like an accordion as carriages 301 move away from each other. The folded sheet may have grooves or holes to allow passage of tools, rails or other devices.

In one embodiment, the tools are concentric tools such that one fits inside another. For example, a guidewire may slide inside a stent which may slide inside a catheter. Therefore, the carriage 301 closest to the opening 102 may grasp the catheter as it passes through, whereas the stent and guidewire pass through the first carriage 301 unaffected. A subsequent carriage 301 may then grasp the stent while leaving the guidewire unaffected. The guidewire may then be grasped by a carriage 301 further from the opening 102, thus passing through the carriages 301 grasping the catheter and the stent. Upon, for example, the stent being grasped, the carriage 301 grasping the stent may move along the rail 305 axis through the user pushing or pulling the stent. Therefore, the stent may move independent of the guidewire and catheter.

Example Carriage for Grasping a Tool

Figure 4:
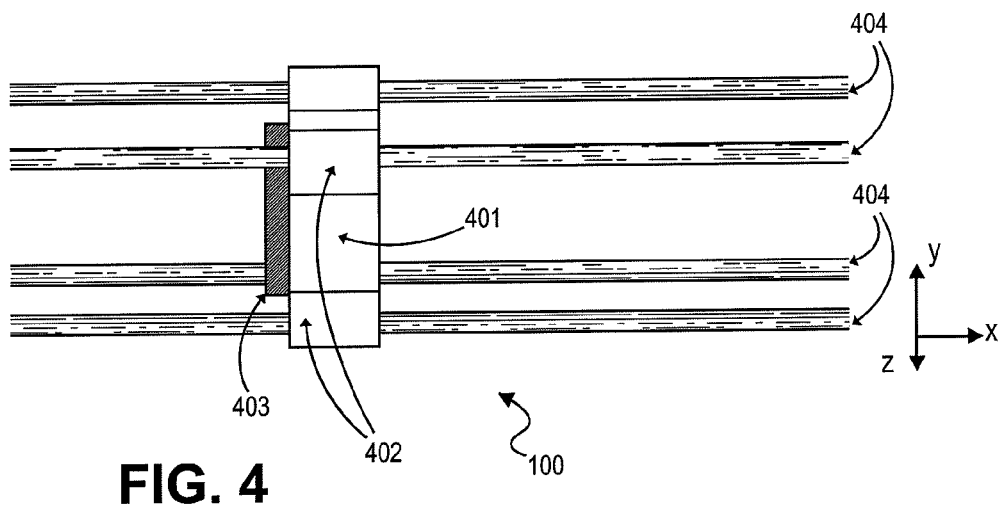
FIG. 4 is a side view of an example carriage 301 in one embodiment of the present invention.

FIG. 4 is a side view of an example carriage 301 of system 100, in one embodiment, for grasping a tool 303 (FIG. 3). In one embodiment, the carriage may include a grasper 401 for grasping a tool, an at least one guide 402 and a sensor 403. Rails 404 are an example orientation of the rails 305 in FIG. 3. As illustrated, the rails 404 may be on four sides of the carriage 301. The guides 402 couple the carriage 301 to the rails 404 and guide the carriage 301 along the rails 404.

In one embodiment, the sensor 403 is configured to sense and identify a tool inserted through the carriage 301. As illustrated, the sensor 403 is positioned on the distal end of the grasper 401. Therefore, a tool being inserted may pass through the grasper 401 before passing through the sensor 403. Hence, upon the sensor 403 identifying the tool, the grasper 401 is able to grasp the tool since the tool is through both the sensor 403 and grasper 401.

Figure 5:
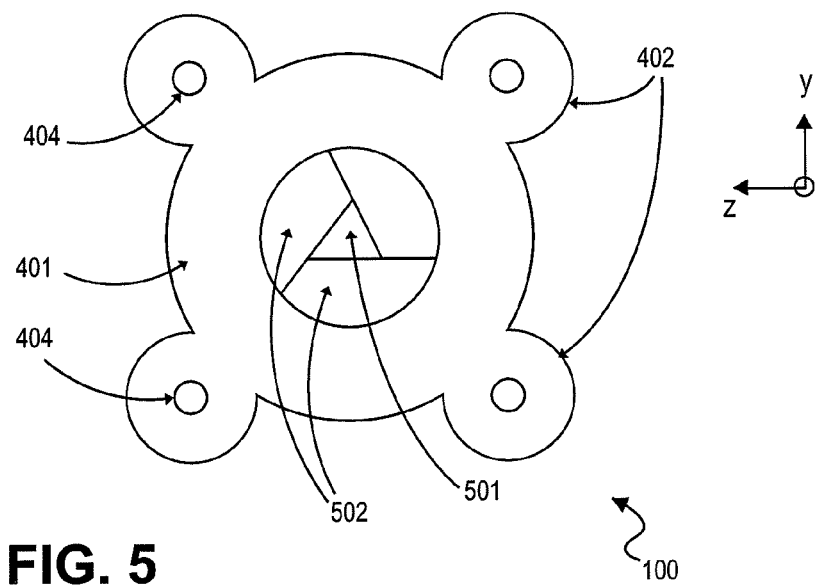
FIG. 5 is a front view (proximal side) of the example carriage 301 of FIG. 4.

FIG. 5 is a front view (proximal side) of the carriage 301 in FIG. 4. The view is of the proximal end of the grasper 401. In one embodiment, the carriage 301 may include an aperture 501 defined by an iris for passage of tools through the carriage. In one embodiment, the grasper 401 may include a plurality of iris petals 502 to define the iris. In order to grasp a tool, the grasper may contract the aperture 501 by moving the iris petals 502. Hence, a tool may be contacted by the grasper at a number of positions equal to the number of iris petals 502. In one embodiment, the iris petals include a rough edge in order to apply friction to the tool when grasped. In another embodiment, the iris petals may include a sharp edge in order to pinch the tool to be grasped. The concentric tools not grasped by the iris petals 502 (i.e., inside the grasped tool) may freely move through the aperture 501 to carriages positioned on the distal end of the illustrated carriage.

Figure 6:
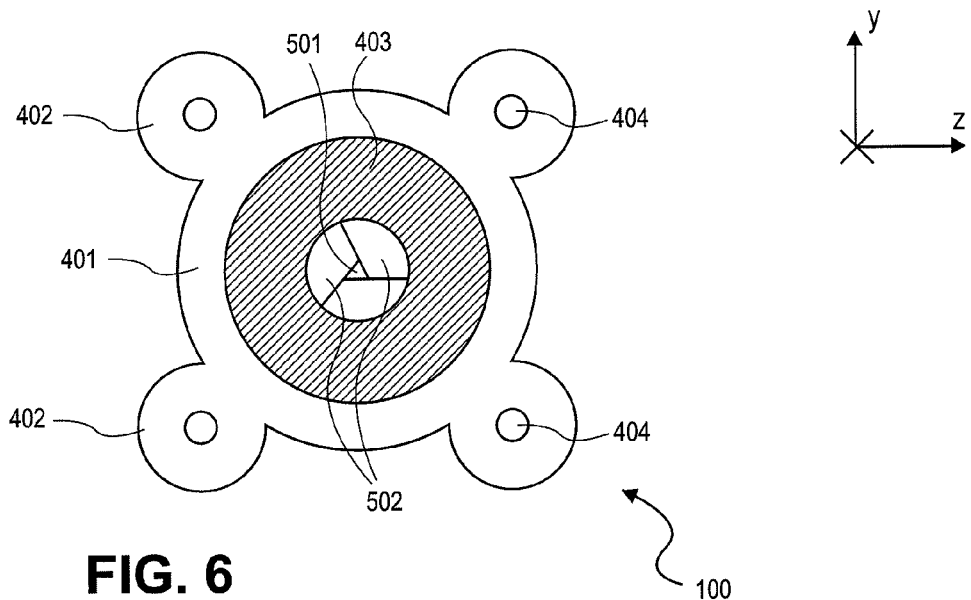
FIG. 6 is a rear view (distal side) of the example carriage 301 of FIG. 4.
Figure 7:
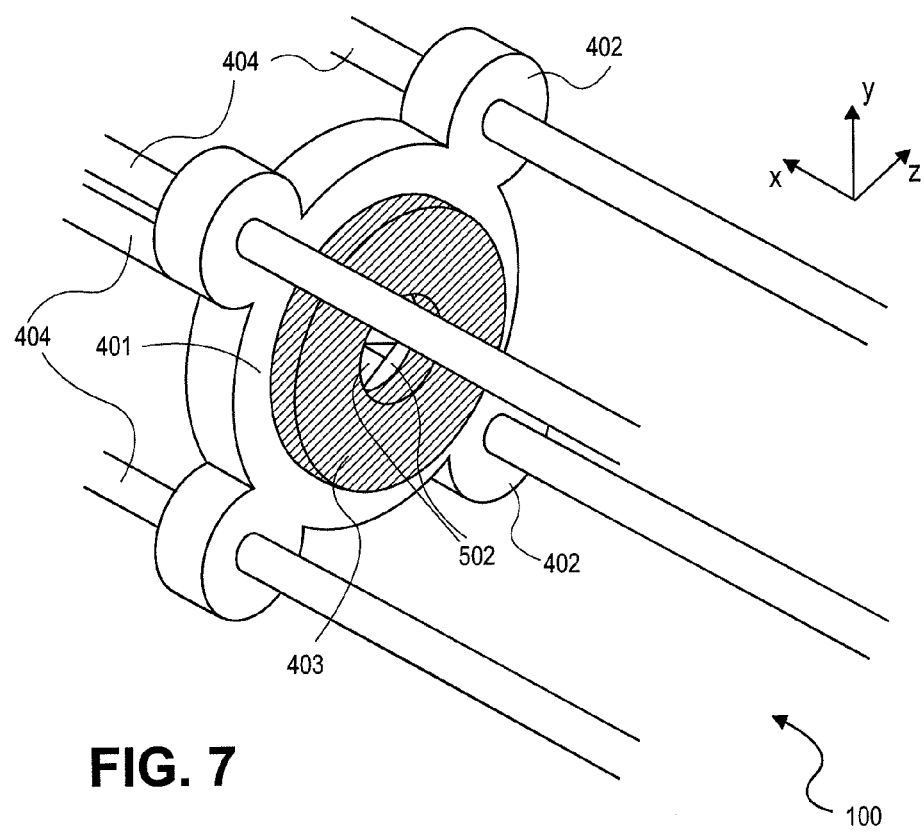
FIG. 7 is a top-right-rear view of the example carriage 301 of FIG. 4.

FIG. 6 is a rear view (distal side) of the example carriage 301 of FIG. 4. The view is of the distal end of the sensor 403 and the grasper 401. As illustrated, the aperture 501 and iris petals 502 are visible through the sensor 403. FIG. 7 is a top-right-rear view of the example carriage 301 in FIG. 4 in order to provide understanding of the orientation of the various portions of the carriage 301.

In one embodiment, the carriages 301 are configured to accept different size tools. For example, carriages 301 further away from the opening 102 of the system 100 may be configured to accept and grasp smaller tools than carriages 301 closer to the opening 102. As a result, the maximum aperture size of the aperture 501 may become smaller as a tool passes through carriages 301 during insertion.

Example Sensor for Identifying a Tool

Figure 8:
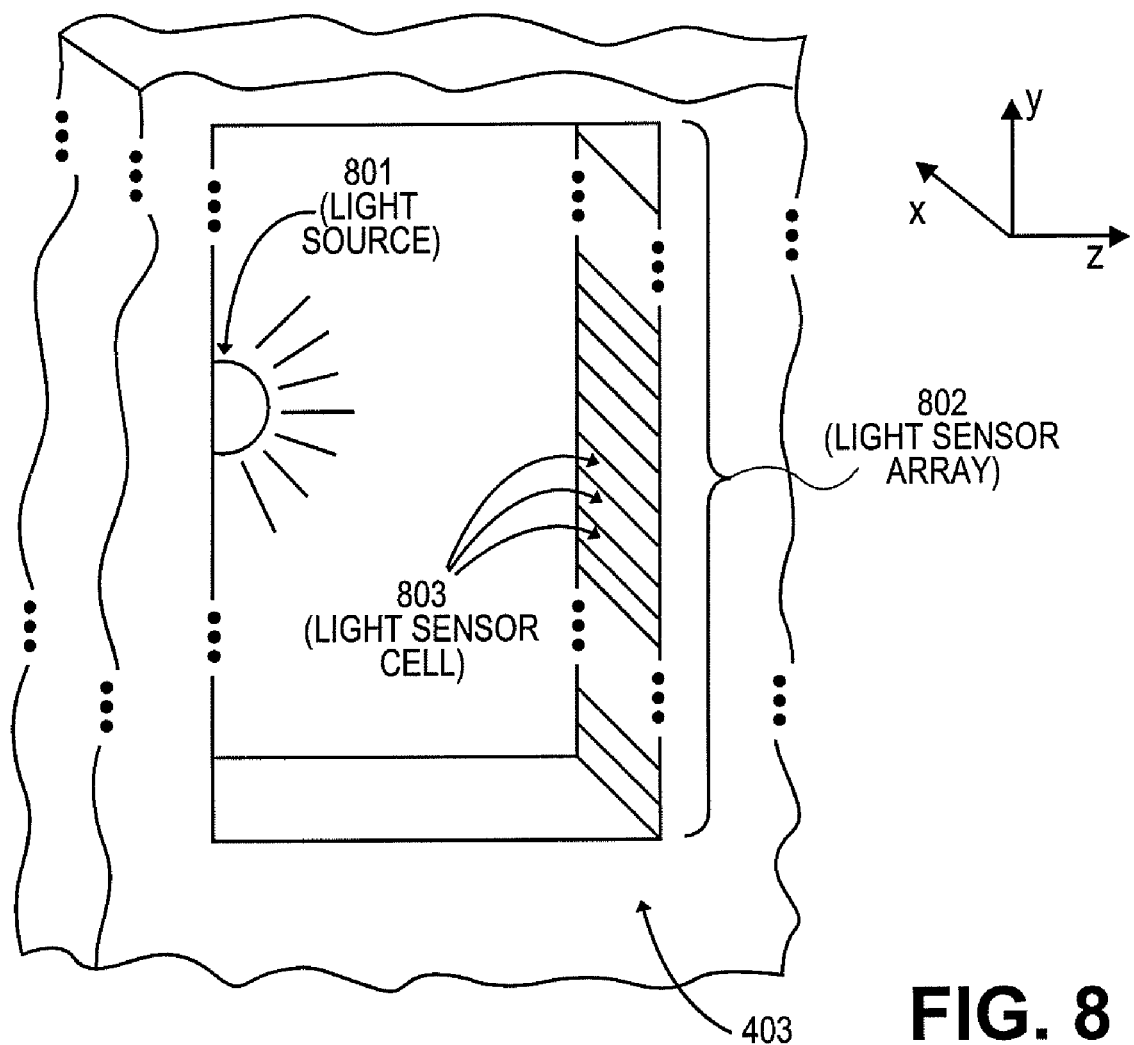
FIG. 8 is a perspective view illustrating an example of a sensor 403 in FIG. 4 in one embodiment of the present invention.

FIG. 8 is a perspective view illustrating an example of a sensor 403 in FIG. 4, in one embodiment, for identifying a tool passing through the carriage. In one embodiment, the sensor 403 is a light and/or optical sensor and may include a light source 801 and a light sensor array 802 (including light sensor cells 803). In one embodiment, the light source is a light emitting diode or a plurality of light emitting diodes positioned on the inside wall of the sensor 403. Other embodiments of light sources, though, include ultraviolet emitters, infrared emitters, a porthole to accept outside light, neon, or a halogen light.

The light sensor array 802 may be a charge coupled device (CCD) including a plurality of sensor pixels (e.g., the light sensor cells 803) to receive light from the light source 801. In one embodiment, the light sensor array 802 is an N×1 arrangement of light sensor cells 803 to measure light received from the light source 801. For example, the light sensor array 802 may be a 256×1 array of cells 803.

Figure 9:
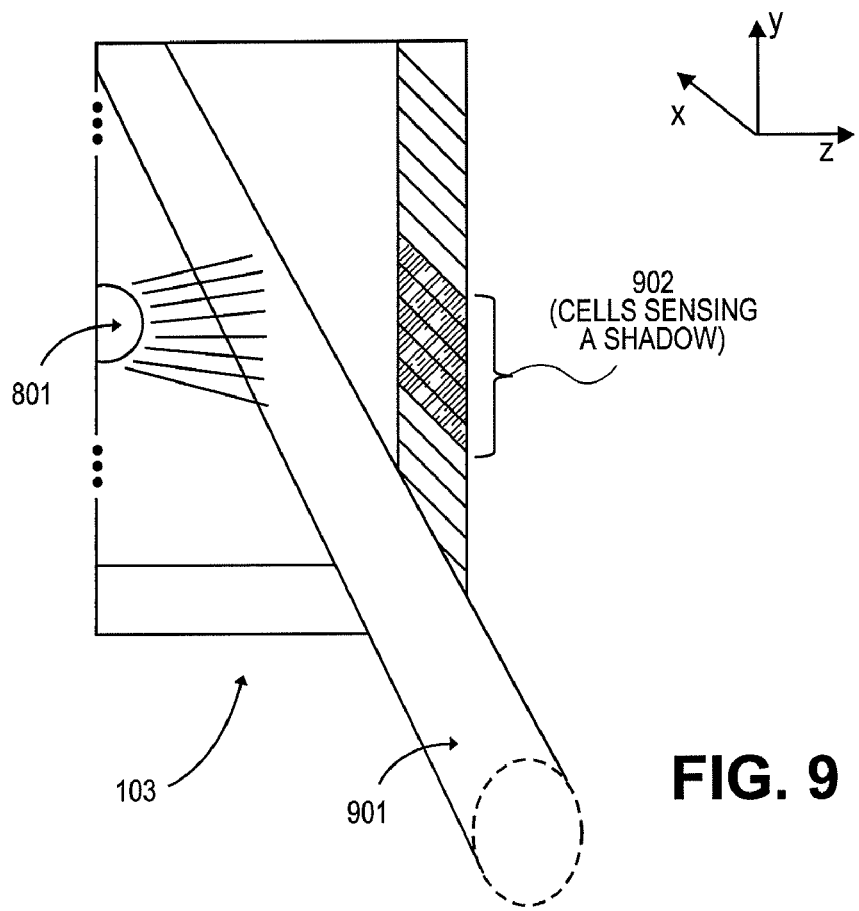
FIG. 9 illustrates the example sensor 403 of FIG. 8 measuring the diameter of a tool.

FIG. 9 illustrates the example sensor 403 of FIG. 8 measuring the diameter of a tool 901. In one embodiment the sensor 403 measures the diameter of the tool 901 in identifying the tool 901. To measure the diameter, the cells 902 may sense a shadow cast by the tool 901. In one embodiment, a shadow is sensed at a cell if the light received at a cell of 902 is less than a predefined threshold value. In another embodiment, the value measured is a drop from a previous measurement at the same cell that exceeds a predefined threshold.

Figure 10:
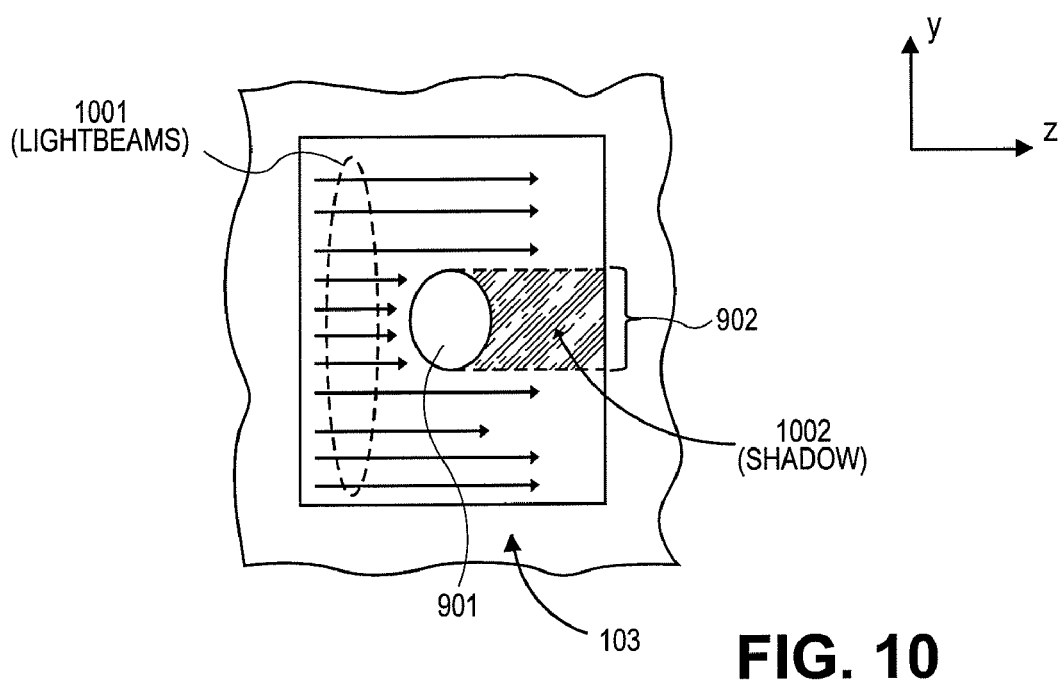
FIG. 10 illustrates an example for measuring the diameter of the tool in FIG. 9.

FIG. 10 illustrates an example for measuring the diameter of the tool 901 in FIG. 9. Some lightbeams 1001 emitted from the light source 801 are blocked by the intruding tool 901, thus casting the shadow 1002 on the cells 902 of the array 802. While the cells 902 may receive reflected light, such as from the walls, the measured light at the cells in 902 is not enough to satisfy the threshold condition. Therefore, the diameter of the tool 901 may be determined by summing the number of pixels 902. Hence, if a catheter is predetermined to approximately be 40 pixels wide, and the number of cells 902 approximately equals 40 when identifying a tool, then the tool 901 is identified as a catheter.

In one embodiment, the sensor 403 periodically senses for a tool (e.g., 20 times a second). In one embodiment, a sensing may be performed with any identification of a tool then performed. The next group of sensing and identifying is then performed. The process may be performed in fast succession in an attempt to estimate performing continuous sensing. As a further result, the sensor 403 may be able to determine changes in measured light at cells between subsequent sensings during identification of a tool, thus identifying a drop in received light at a cell.

While the inside walls of the sensor 103 are illustrated as a parallelogram or curve in the Figures, the orientation of the walls is not important as long as the sensor is able to identify the tool 901. Furthermore, while the sensor 103 is described as a light sensor, other embodiments of sensors include, but are not limited to, RFID tag readers, barcode scanners, optical sensors, or other sensors that do not physically contact the tool 901.

Example Guide for Movement of the Carriage

Figure 11:
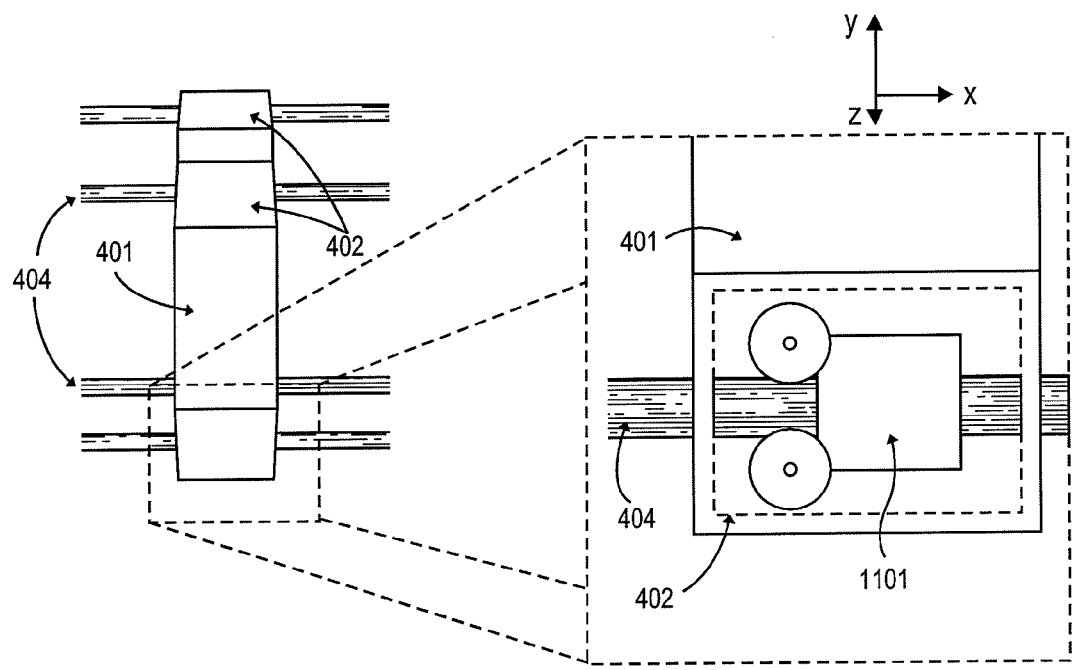
FIG. 11 is an exploded, cut-out view of an example guide 402 of the example carriage 301 in FIG. 4.

FIG. 11 illustrates an exploded, cut-out view of an example guide 402, in one embodiment, of the example carriage 301 in FIG. 4. In one embodiment, the guide 402 may comprise a coupler 1101 to couple the carriage 301 to a rail 404. In one embodiment, the coupler 1101 may be a bearing system or wheels to reduce friction between the rail 404 and the carriage 301. In another embodiment, the coupler 1101 may further comprise a motor alternative or in addition to the plurality of motors 202 (FIG. 2) in order to assist in providing haptic effects (e.g., vibrations, assisted movement of the carriage, resistance) to the user through the grasped tool. Therefore, as the carriage 301 moves along rails 404, the coupler 1101 may engage the rail 404, rolling its bearings or a wheel against the rail 404. In addition, the coupler 1101 may be able to sense changes in force against the rail in order to determine if a haptic effect is to be provided.

Second Sensor of the Carriage

Figure 12:
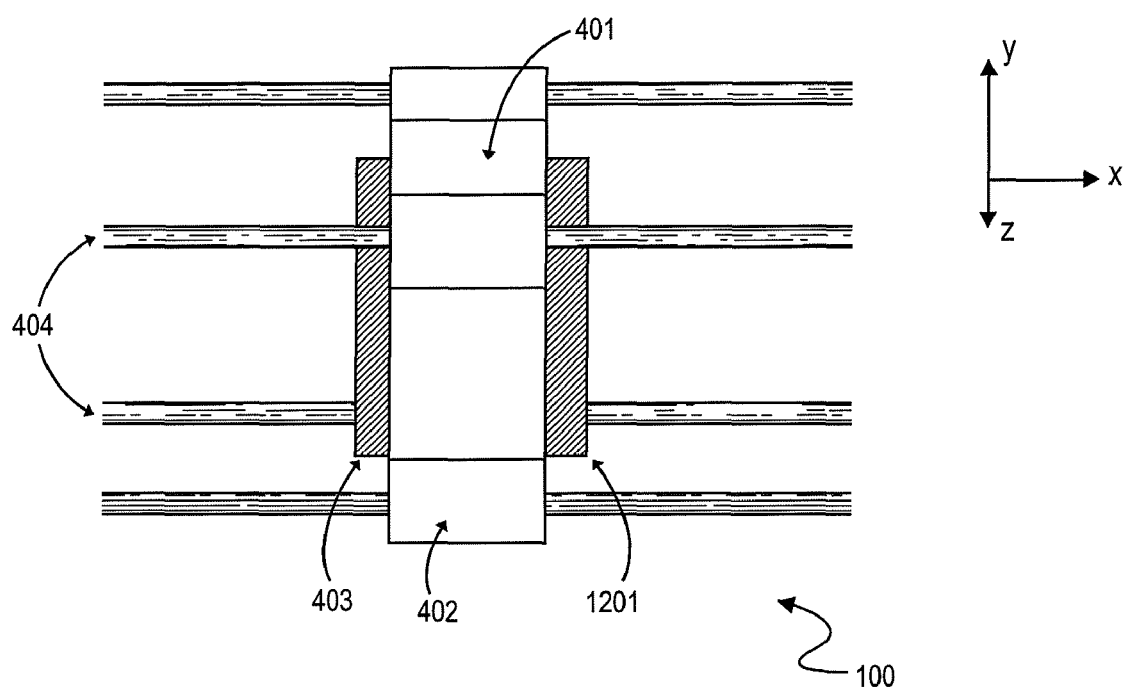
FIG. 12 is a side view of the another embodiment of the example carriage 301 of FIG. 4 comprising an additional sensor.

FIG. 12 illustrates another embodiment of a carriage, and is a side view of the example carriage 301 of FIG. 4 comprising an additional sensor 1201. As illustrated, the sensor 1201 is coupled to the proximal end of the grasper 401. Therefore, a sensor exists on both ends of the grasper 401. In one embodiment, the sensor 1201 is similar to sensor 403, thus identifying a tool before the sensor 403 identifies the tool during the tool's insertion. In one embodiment, a diameter is measured/ identified by the sensor 1201 and a diameter is measured/identified by the sensor 403. In one embodiment, the system 100 determines if the tool measured at each sensor 403, 1201 is the same tool by comparing the measured diameters. If both sensors identify the correct diameter of the tool to be grasped by the grasper 402, then the grasper 401 grasps the tool hv contracting the aperture 501.

In one embodiment, if the measured diameters do not match between the two sensors, then the two sensors may be identifying different tools. For example, if a catheter is through the proximal sensor 1201 but has not reached the distal sensor 403, then the proximal sensor 1201 may determine and the distal sensor 403 may not determine the diameter of the catheter. If a guidewire inside the catheter has passed through both sensors, then the distal sensor 403 may determine the diameter of the guidewire, which is smaller than the catheter. As previously stated, the proximal sensor 1201 is measuring the diameter of the catheter. Therefore, the two sensors are identifying different tools. As a result, if the carriage is assigned the catheter to grasp, the sensor waits for the catheter to pass through the distal sensor 403 by waiting for the distal sensor 403 to identify the catheter instead of the guidewire. As a result, upon the diameters matching between the two sensors and matching the diameter of the catheter, the carriage 301 then grasps the catheter.

Proximity Sensor of the Carriage

In one embodiment, the system 100 also automatically releases a grasped tool during the tool's removal from the system 100. In one embodiment, a carriage 301 grasps a tool when positioned at a home position along the rails 404. The carriage 301 may then be displaced from the home position during movement of the tool. Therefore, in one embodiment, the carriage 301 is to release the tool when the carriage 301 returns to the home position. In another embodiment, the carriage 301 is configured to release a grasped tool upon coming within a predefined distance of another carriage on the proximal side of the carriage 301. As a result, in one embodiment, the carriages 301 include a proximity sensor or other device for the system 100 to determine when to release a grasped tool.

Figure 13:
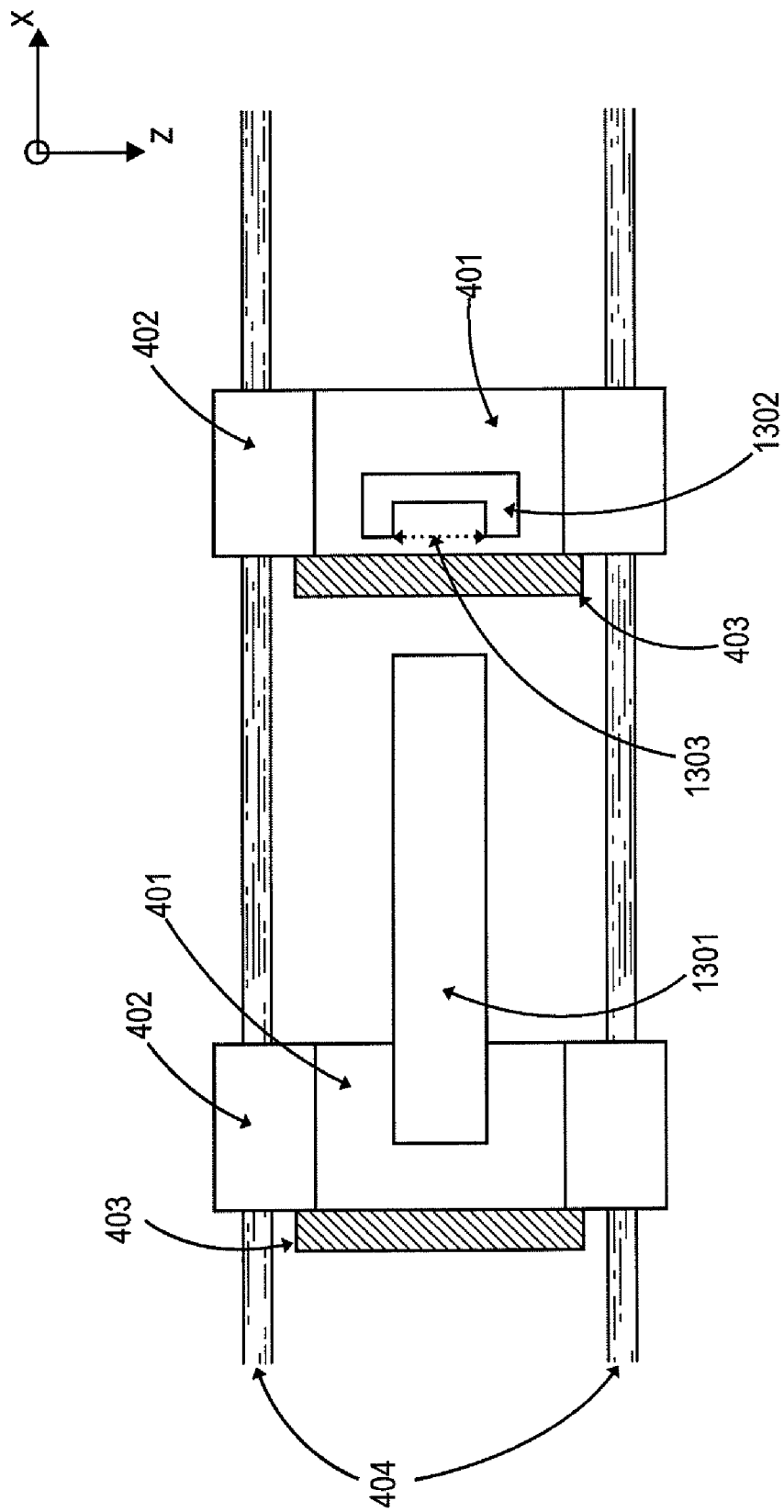
FIG. 13 is a top view of another embodiment of two example carriages 301 for the system in FIG. 2, wherein the two example carriages 301 include an example proximity sensor.
Figure 14:
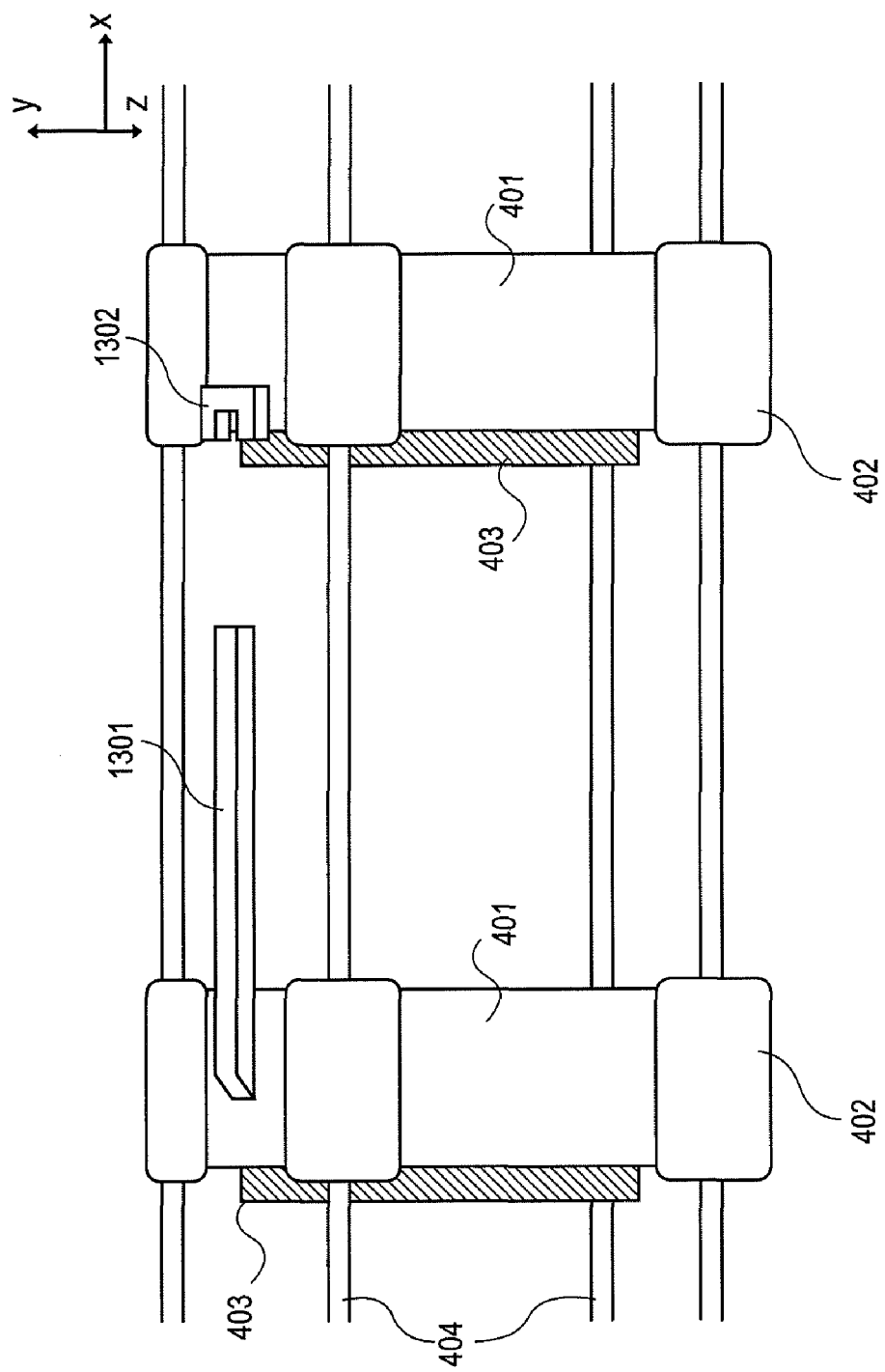
FIG. 14 is a side view of the two example carriages 301 in FIG. 13.

FIG. 13 is a top view of another embodiment of the two example carriages 301 of the system 100 in FIG. 2, wherein the two example carriages 301 include an example proximity sensor. FIG. 14 is a side view of the two example carriages 301 in FIG. 13. In FIGS. 13 and 14, the proximity sensor may include a prong 1301 and a receptor 1302 that emits a beam 1303. In one embodiment, when the two carriages approach each other, the prong 1301 splits the beam 1303 of the receptor 1302. As a result, the system 100 may determine that the two carriages are a predefined distance apart and thus determine that the grasped tool in the distal carriage 301 is to be released. As previously stated, in one embodiment, the minimum distance between carriages may be the distance between carriages so that they do not interfere with the operation of other neighboring carriages. In another embodiment, the minimum distance may be a predefined distance in order to allow a developer or user to determine the position of the carriages relative to one another. In one embodiment, the proximity sensor is included in the assembly 302 (FIG. 3).

In one embodiment, when the two carriages are a predefined distance apart such that the prong 1301 splits the beam 1303, the distal carriage of the two carriages 301 is in a home position. In one embodiment, home position of a carriage may be the initial position of a carriage before grasping a tool and being displaced. For example, the proximal carriage may approach its home position before the distal carriage. Therefore, the home position of the distal carriage (the position where it grasped the tool) is the predefined distance from the home position of the proximal carriage. In another embodiment, the home position for the first carriage closest to the opening 102 (FIG. 2) is a predefined distance from a fixed portion of the system 100. As a result, the home position of the next carriage may be a predefined distance from the home position of the first carriage, and the home position of the next carriage may be two times the predefined distance from the first carriage's home position.

In another embodiment of the proximity sensor, the proximity sensor may identify the carriages position on the rail(s) 305, thus determining the home position for each carriage according to the determined displacement from observing the rail. For example, the sensor may be an optical sensor to capture an image, a carriage's home position is painted on the rail using a specific color, and therefore a control circuit identifies the home position from a captured image by identifying the color on the rail.

Example Illustration of the Exemplary System

Figure 15:
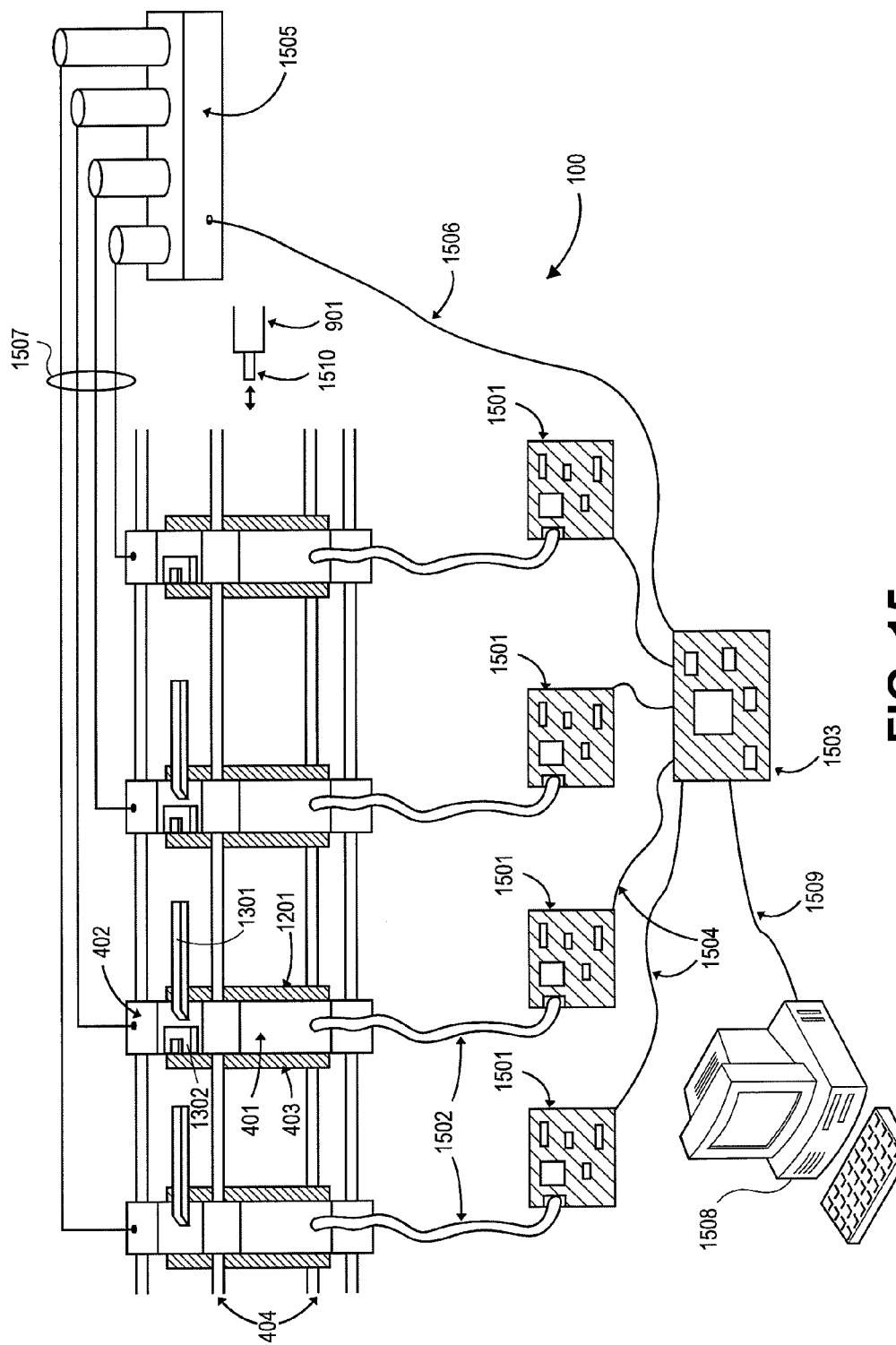
FIG. 15 illustrates one embodiment of the example system 100 in FIG. 2, including four example carriages 301.

FIG. 15 illustrates one embodiment of the example system 100 in FIG. 2, including four carriages 301 to accept inserted tools to the system 100. In the example, each carriage may comprise a grasper 401, guide(s) 402 to guide along rails 404, proximal sensor 1201, distal sensor 403, and a proximity sensor (1301-1303). In one example of the system 100, the carriages 301 include a control circuit 1501 communicably coupled (1502). In one embodiment, the control circuit 1501 receives the sensing data from the sensors 403, 1201, determines the diameter of a sensed tool, compares if the diameter is approximately the same between the two sensors, identifies the tool as to be grasped by the grasper 401, and controls the grasper 401 to grasp the tool.

In one embodiment, the system 100 may further include a main control circuit 1503 coupled (1504) to the control circuits 1501 for controlling the distance relationships between the carriages 301, determine when to release a tool, determine when to supply haptic effects, accept inputs from a user in initializing the system 100, determine if a malfunction exists (e.g., an incorrect tool is inserted), or control other feedback to be sent to the user during simulation. In one embodiment, the main control circuit 1503 is coupled (1509) to a user interface 1508 to receive inputs from and provide feedback to a user. The main control circuit may also be coupled (1506) to motors 1505 (e.g., motors 202), which are attached (1307) to the carriages 301 in order to provide haptic effects through the tools (901, 1510) to the user.

In one embodiment, the control circuits 1501 and the main control circuit 1503 may be combined (e.g., circuit 203 of FIG. 2). In addition, feedback given to the user may be visual such that the system 100 displays on the user interface 1508, for example, the inside of a person during simulation, thus making the simulation more immersive. In another embodiment, the visual simulation is provided by a virtual scannings device and display that approximates the scanning and display devices used in actual medical operations.

The exemplary methods below are described in relation to the example system 100 illustrated in FIG. 15.

Method for Initializing the Medical Simulation System

In one embodiment of the system 100, the system 100 determines if an incorrect tool is inserted. As a result, the system 100 may prompt the user with an error and request the user to remove the incorrect tool. To do so, in one example, one of the sensors of the carriages 301 may determine that the diameter of the tool does not match the diameter of any tool to be used during the simulation. Hence, the system 100 may know which tools are to be received and rejects instruments that are not identified as one of the known tools. In order to properly identify tools inserted into the system 100, the system may be initialized by a user to simulate a specific medical procedure.

Figure 16:
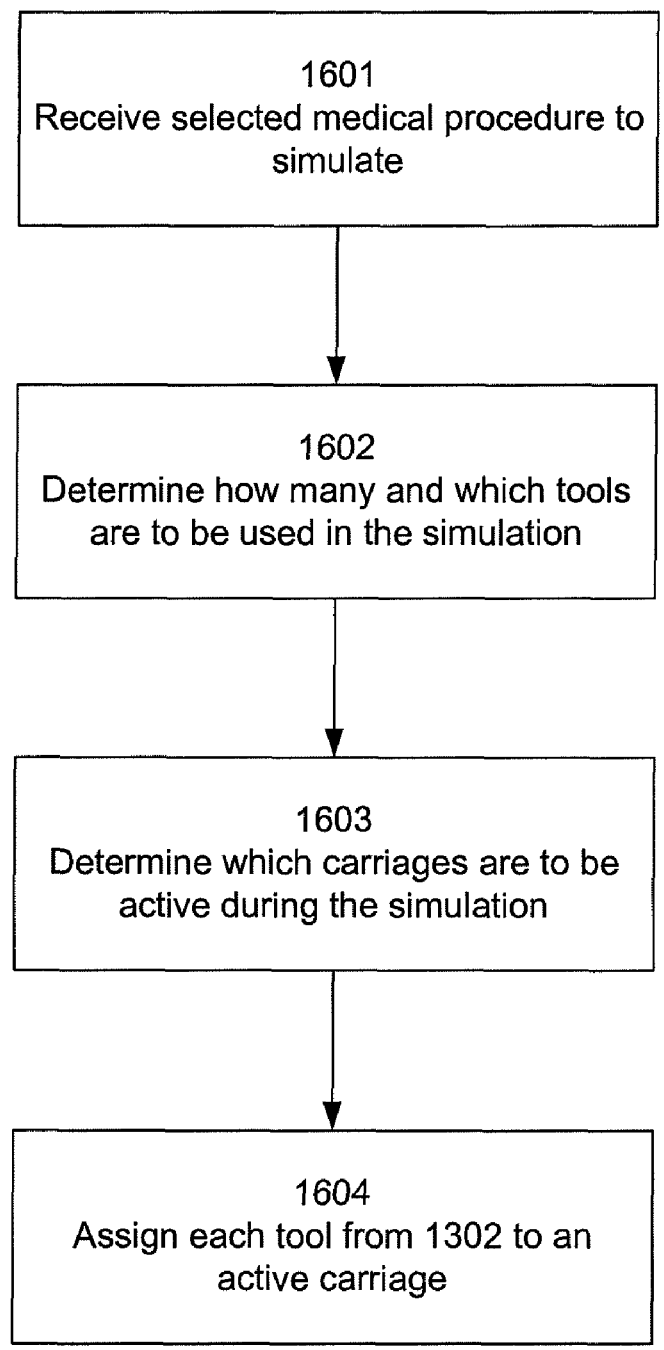
FIG. 16 illustrates an exemplary method for initializing the medical simulation system 100 of FIG. 15 to simulate a predetermined medical procedure.

FIG. 16 illustrates an exemplary method for initializing the medical simulation system 100 of FIG. 15 to simulate a predetermined medical procedure. Beginning in 1601, the system 100 receives the medical procedure to be simulated. In one embodiment, the user indicates through the user interface 1508 which medical procedure is to be simulated (e.g., stenting a blood vessel). Proceeding to 1602, the system 100 determines which and how many tools are to be used in the simulation defined in 1601. In one embodiment, the system 100 may have a storage saving a list of tools for each selectable simulation. In another embodiment, the user may input which tools are to be used in the procedure.

Proceeding to 1603, the system 100 may determine which carriages are to be active during the simulation. For example, if three tools are to be used, then three carriages are used to grasp the three tools. Since the carriages 301 may include differing maximum apertures 501, the carriages may each be for a specific type (or size) of tool. Therefore, the carriage for the type of tool not selected for the medical simulation may not be active for the medical simulation. For example, the carriage farthest from the opening 102 may be configured to accept a guidewire. If the selected procedure, for some reason, does not use a guidewire, then the fourth carriage may be inactive for the simulation. In another embodiment, all carriages are active, and all sensors are configured to identify tools inserted into the system 100.

Upon determining in 1603 which carriages 301 are to be active, the system 100 assigns a tool determined in 1602 to a carriage 301 determined active in 1603. Thus, in one embodiment of the simulation, the carriage 301 assigned to a specific tool may grasp the tool when the carriage 301 identifies the tool as inserted through the carriage 301.

In another embodiment, a medical tool may be identified by a user immediately before insertion during simulation. Each carriage 301 may be configured to grasp a tool within a predefined range of diameters. Therefore, the carriage 301 identifying the diameter of the inserted medical tool as within its predefined range of diameters grasps the medical tool.

Method for Grasping the Tools During a Simulation of a Medical Procedure

Figure 17:
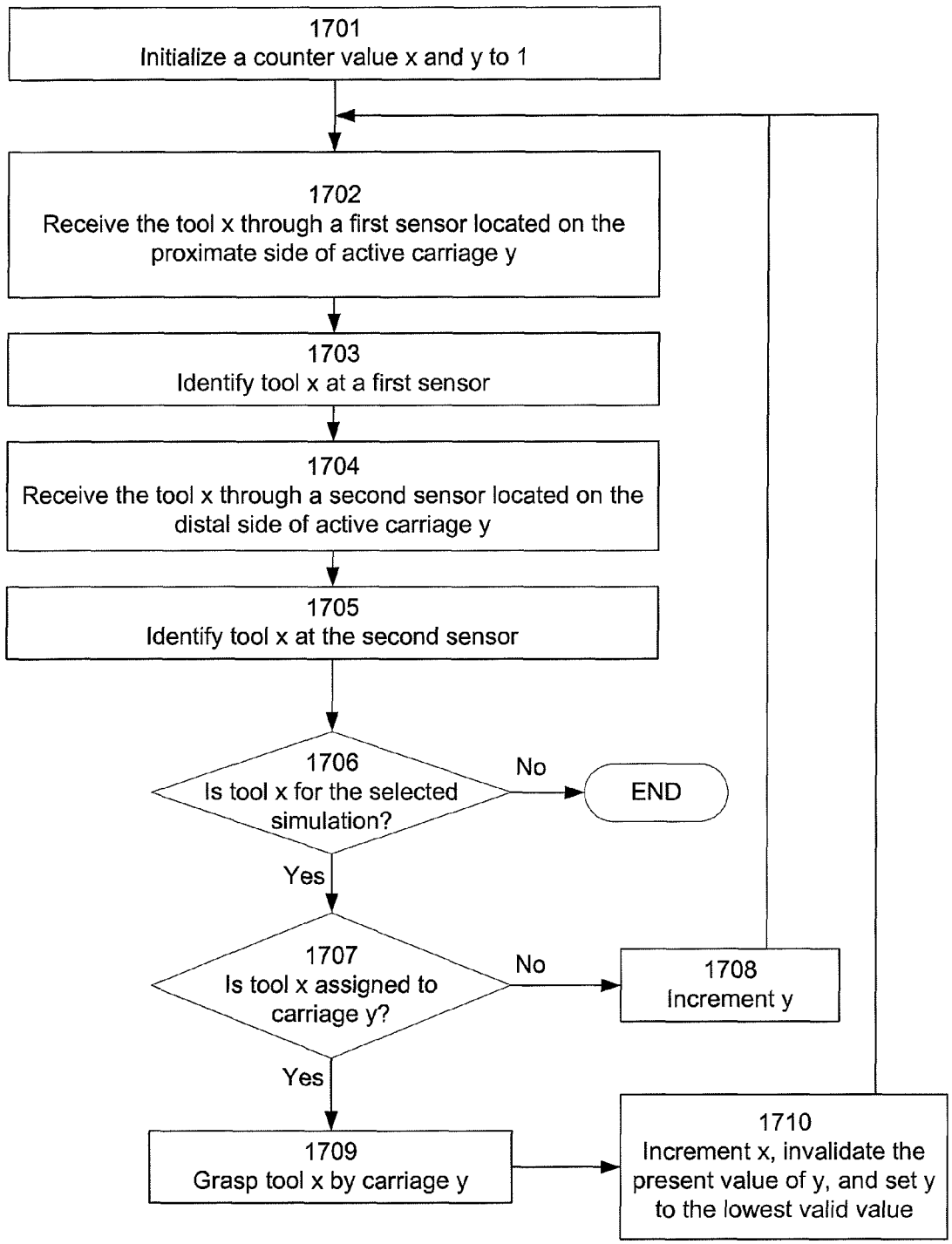
FIG. 17 illustrates an example method of the system 100 of FIG. 15 to automatically identify and grasp the tools inserted into the system 100 by a user.

FIG. 17 illustrates an example method of the system 100 of FIG. 15 to automatically identity and grasp the tools inserted into the system 100 by a user. Beginning at 1701, a counter x and a counter y may be initialized to one. In one embodiment, the counters are to identify which carriage is identifying and/or grasping which tool during the procedure until all tools are grasped. Proceeding to 1702, the system 100 receives an inserted tool x through a proximal sensor 1201 of active carriage y. For example, a first tool (e.g., guidewire) may be inserted through the proximal sensor of carriage 1. In one embodiment, the carriage numbers do not specify a specific sequence or position of the carriages. Therefore, carriage 1 may be any of the active cam ages.

Proceeding to 1703, the tool x is identified by the proximal sensor of the carriage y. The tool x is then received through a distal sensor 403 of active carriage y in 1704. Proceeding to 1705, the tool x is identified by the distal sensor in 1705. In 1706, the system 100 determines if identified tool x (by both sensors) is for the predefined/selected simulation. In one embodiment, the system looks up the tool diameter in the stored diameters of the list of tools for the selected simulation. If tool x is not for the selected simulation, then the process may end with the system 100 identifying an incorrect tool for the procedure. In one embodiment, an error message may be presented to the user via the user interface 1508.

If tool x is determined to be for the selected simulation in 1706, then the system further determines if the tool x is assigned to carriage y. If tool x is not assigned to carriage y, then tool x is not to be grasped by carriage y. Therefore, y is incremented in 1708 and process reverts to 1702. As a result, the system 100 proceeds through the process of FIG. 17 until determining which carriage is to grasp tool x.

If tool x is assigned to carriage y in 1707, then the carriage y grasps tool x in 1709. Upon tool x being grasped by carriage y, carriage y does not grasp another tool. Therefore, the system 100 may not observe present carriage y in determining which carriage is to grasp the next tool. As a result, in 1710, x is incremented, the present value of y is invalidated for the counter, and y is set to the lowest valid value for the counter. For example, if tool 1 is grasped by carriage 3, then x is incremented to 2, the y counter is modified such that y is not able to equal 3, and the y counter is set to 1. Therefore, if incrementing y when y equals 2, the counter y is set to 4 (skipping the invalid value of 3).

Upon all active carriages grasping a tool in 1709, the process ends. Upon the system 100 grasping all of the inserted tools, in one embodiment, the system may implement other parts of the medical simulation, such as providing haptic effects to the user through the tools and other feedback through the user interface 1508 as necessary until the user removes the tools from the system 100.

In another embodiment, while the example method describes identifying tools one by one, all active carriages may also be identifying any inserted tools simultaneously. Therefore, in one example, two carriages may be identifying and grasping different tools at the same time. In a further embodiment, a medical tool may be removed before another is inserted or two medical tools may be inserted at approximately the same time so that carriages are identifying more than one tool at once. For example, a catheter for a guidewire may be released by a carriage and removed from the system 100 before a different catheter with a stent is inserted into the system 100.

Figure 18:
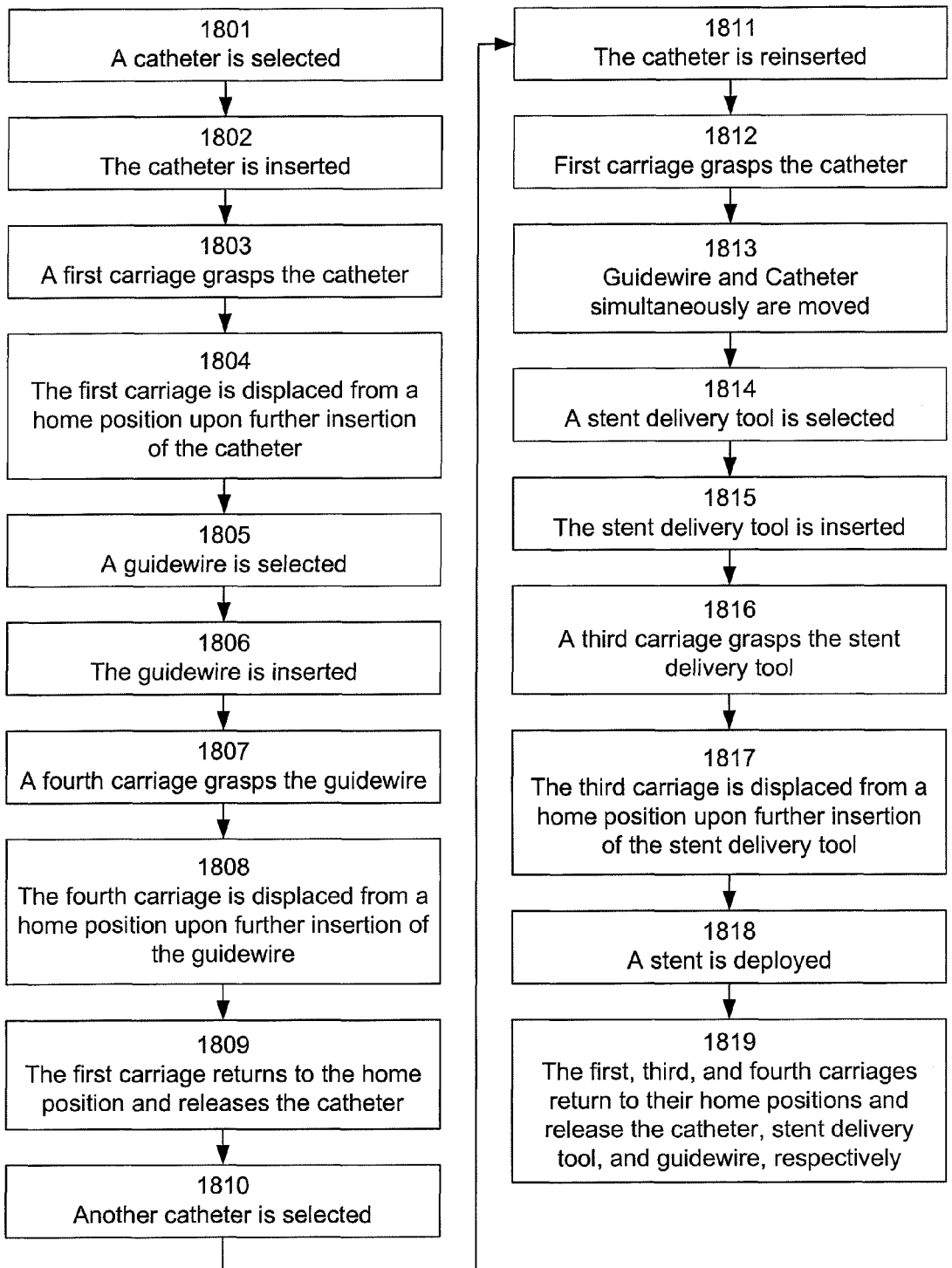
FIG. 18 illustrates an example interaction between the system 100 of FIG. 15 and a user during an example simulation of stenting an artery.

FIG. 18 illustrates an example interaction between a user and the system 100 where an example medical operation of stenting an artery is performed. Beginning at 1801, a catheter is selected for the simulation. In one embodiment, the user selects the catheter from a list of medical tools on a display of the system. Upon selecting the catheter, the user may insert the catheter into the system 100 in 1802. The catheter may be an actual catheter or a proxy catheter specific to the simulation system 100. Proceeding to 1803, the first carriage grasps the inserted catheter. In one embodiment for determining that the first carriage grasps the catheter, the sensors of the first carriage may identify that the diameter of the catheter is within a range of diameters of medical tools to be grasped by the first carriage.

Proceeding to 1804, the first carriage is displaced from a home position. During a simulation, the user may push the catheter further into the system 100 to simulate pushing the catheter further into the artery of a human body in order to approach a target location in the artery to be stented. Hence, as the catheter is pushed into the system 100, the first carriage grasping the catheter is displaced. A guidewire may then be selected as a new medical tool for insertion in 1805. In one embodiment, the user selects the guidewire from a list of medical tools to be used. Upon selection of a guidewire, the guidewire may be inserted by a user into the system 100 in 1806. As with the catheter, the guidewire may be an actual guidewire or a proxy guidewire specific to the simulation system 100.

Proceeding to 1807, the fourth carriage grasps the guidewire. In one embodiment, the guidewire passes through the first through third carriages to reach the fourth carriage. In doing so, the first through third carriages may identify the tool and determine that the tool is not to be grasped by the carriage. The guidewire is then identified by the fourth carriage as to be grasped by the fourth carriage. Upon grasping the guidewire, the fourth carriage may be displaced from a home position in 1808 as the guidewire is further inserted into the system 100. The user further inserting the guidewire simulates the guidewire being pushed through an artery to reach a location in the artery for stenting.

After a user is finished with the catheter being grasped by the first carriage, the user may remove the catheter in 1809. In one embodiment, as the user pulls out the catheter, the first carriage returns to a home position. Upon the first carriage returning to a home position, the first carriage may release the catheter, thus allowing the user completely to remove the catheter from the system 100.

Proceeding to 1810, the user may wish to insert another catheter. Therefore, another catheter is selected in 1810. Upon selection of the catheter in 1810, the catheter may be reinserted into the system 100 in 1811. In another embodiment, a different catheter may be inserted into the system instead of the same catheter being reused. Upon inserting the catheter in 1811, the first carriage may grasp the catheter in 1812. The guidewire and the catheter may then be moved simultaneously by the user in 1813 in simulating placing the guidewire and catheter in position for stenting the artery. As the guidewire and catheter are moved, the first and fourth carriages are displaced within the system 100.

Upon positioning the guidewire and catheter, a stent delivery tool may be selected by the user next to be inserted into the system 100 in 1814. Upon selection of the stent delivery tool in 1814, the user may insert the stent delivery tool into the system 100 in 1815. Proceeding to 1816, the third carriage grasps the stent delivery tool. In one embodiment, the first and/or second carriage determine the diameter of the stent delivery tool as outside the range of diameters for the first or second carriages while the third carriage determines the diameter to be within its range of diameters. Upon grasping the stent delivery tool in 1816, the third carriage may be displaced from a home position as the user further inserts the stent delivery tool into the system 100. For example, pushing the stent delivery tool further into the system 100 simulates positioning the stent delivery tool in an artery for deployment of the stent.

Proceeding to 1818, a stent is deployed from the stent delivery tool in simulating stenting an artery. In one embodiment, a stent may be virtually deployed instead of physically deployed. For example, the system 100 simulates for the user a deployment of a stent, but no stent is physically deposited into the system 100.

Upon deploying the stent in 1818, the user may wish to remove the catheter, stent delivery tool, and guidewire from the system 100 to conclude the medical simulation. Therefore, in the process of removing the medical tools from the system 100, the first, third, and fourth carriages may be returned to their respective home position. Upon returning to their home positions, the first, third, and fourth carriages may release the catheter, stent delivery tool, and guidewire, respectively, so that the user may remove the medical tools in their entirety from the system 100 in 1819 and conclude the simulation.

FIG. 18 is merely for explanation purposes and to illustrate that simulations may include a variety of insertion and removal of medical tools during random times of the simulation. As a result, FIG. 18 may not include all processes for the example simulation, not require all illustrated processes of the example simulation, and not require a specific order for the processes as certain processes may occur in a different order.

General

Modules of the different embodiments of the described system 100 may include software, hardware, firmware, or any combination thereof. The modules may be software programs available to the public or special or general purpose processors running proprietary or public software. The software may also be specialized programs written specifically for image manipulation. For example, the control circuit(s) may be a general processor running an application or an embedded circuit performing predefined routines.

For the exemplary methods illustrated in FIGS. 16 and 17, embodiments of the invention may include the various processes as set forth above. The processes may be embodied in computer-executable instructions which cause a general-purpose or special-purpose processor to perform certain steps. Alternatively, these processes may be performed by specific hardware components that contain hardwired logic for performing the processes, or by any combination of programmed computer components and custom hardware components. Furthermore, embodiments of the invention may not require all of the various processes presented, and it may be conceived by one skilled in the art as to how to practice the embodiments of the invention without specific processes presented or with extra processes not presented.

Elements of the present invention may also be provided as a computer-readable medium for storing the computer-executable instructions. The computer-readable medium may include, but is not limited to, floppy diskettes, optical disks, CD-ROMs, and magneto optical disks. ROMs, RAMs, EPROMs, EEPROMs, flash, magnetic or optical cards, propagation media or other type of media/computer-readable medium suitable for storing electronic instructions. For example, identifying a tool may include receiving inputs from sensors and executing an application using the inputs.

The foregoing description of the embodiments of the invention has been presented only for the purpose of illustration and description and is not intended to be exhaustive or to limit the invention to the precise forms disclosed. Numerous modifications and adaptations are apparent to those skilled in the art without departing from the spirit and scope of the invention. For example, while four carriages are illustrated, any number of carriages may exist in the system. In another example, while the carriages are described as running along rails, walls, magnets, or other devices may be used to direct movement of the carriages. In addition, a separation of objects using magnets or other forms of reducing resistance during coupling of devices may be used to reduce friction between the carriages and the rails. In another example, while an iris has been described for grasping a tool, other grasping devices may be used, including, but not limited to, a claw, wedge, suction, or other force. In another example, while the rails have been described as being on four sides of a carriage, any number and positioning of rails may be used to direct the axis of movement for a carriage.

What is claimed is:

1. A device comprising:
a first grasper comprising a first grasper proximal end and a first grasper distal end;
a first sensor coupled to the first grasper distal end and configured to identify a first medical tool approaching the first sensor, wherein the first grasper is configured to automatically grasp the first medical tool upon the first sensor identifying the first medical tool; and
an actuator configured to provide a haptic effect to a user of the device.

2. The device of claim 1, wherein the first sensor being configured to identify the first medical tool comprises the first sensor being configured to identify the diameter of the first medical tool.

3. The device of claim 2, wherein the first sensor comprises an optical sensor.

4. The device of claim 3, wherein the first sensor comprises a light source and a plurality of light sensor cells configured to receive light from the light source.

5. The device of claim 4, wherein the diameter of the first medical tool is related to the number of sensor cells not receiving light from the light source.

6. The device of claim 1, further comprising a second sensor coupled to the first grasper proximal end and configured to identify the diameter of the first medical tool approaching the second sensor before the first sensor identifies the first medical tool.

7. The device of claim 6, wherein the second sensor comprises an optical sensor.

8. The device of claim 7, wherein the second sensor comprises a light source and a plurality of light sensor cells configured to receive light from the light source.

9. The device of claim 8, wherein the diameter of the first medical tool is related to the number of sensor cells not receiving light from the light source in the second sensor.

10. The device of claim 8, wherein the first sensor and the second sensor being configured to identify the first medical tool further comprises being configured to determine whether the diameter identified by the first sensor is approximately equal to the diameter identified by the second sensor.

11. The device of claim 10, wherein the first grasper is configured not to grasp the first medical tool if the diameter identified by the first sensor is not equal to the diameter identified by the second sensor.

12. The device of claim 1, further comprising:
a second grasper comprising a second grasper proximal end and a second grasper distal end; and
a third sensor coupled to the second grasper distal end and configured to identify a second medical tool, wherein the second grasper is configured to automatically grasp the second medical tool upon the third sensor identifying the second medical tool.

13. The device of claim 12, further comprising a fourth sensor coupled to the second grasper proximal end and configured to identify the second medical tool approaching the fourth sensor before the third sensor identifies the second medical tool.

14. The device of claim 1, wherein a first carriage comprises the first grasper and the first sensor and the first carriage comprises a guide configured to guide movement of the first carriage from a home position during displacement of the first carriage if the first carriage is grasping the first medical tool.

15. The device of claim 14, wherein the first carriage comprising the guide further comprises a location sensor to determine whether the first carriage is or is not in the home position, wherein the first grasper of the first carriage comprising the guide is further configured to release the first medical tool upon the location sensor determining the carriage is in the home position.

16. The device of claim 4, wherein:
the plurality of light sensor cells comprise a charge coupled device; and
the light source comprises at least one light emitting diode (LED).

17. A method for simulating a medical procedure, comprising:
receiving a first medical tool at a first grasper proximal end of a first grasper of a first carriage;
receiving the first medical tool through the first grasper past a first grasper distal end of the first grasper;
receiving the first medical tool through a first sensor coupled to the first grasper distal end;
identifying the first medical tool by the first sensor;
grasping the first medical tool by the first grasper upon the first sensor identifying the first medical tool; and
providing a haptic effect to a user by an actuator coupled to the first grasper.

18. The method of claim 17, further comprising:
receiving the first medical tool through a second sensor coupled to the first grasper proximal end; and
identifying the first medical tool by the second sensor before the first sensor identifies the first medical tool.

19. The method of claim 18, wherein identifying the first medical tool comprises determining a diameter of the first medical tool.

20. The method of claim 19, wherein grasping the first medical tool by the first grasper upon the first sensor identifying the first medical tool comprises:
determining whether the diameter from the first sensor is approximately equal to the diameter from the second sensor;
determining whether the diameter from the first sensor and the diameter from the second sensor are approximately equal to a predefined diameter of the first medical tool; and
grasping by the first grasper the first medical tool upon determining the diameter from the first sensor and the diameter from the second sensor are approximately equal to the predefined diameter of the first medical tool.

21. The method of claim 19, wherein determining the diameter of the first medical tool comprises measuring a shadow cast by the first medical tool on a light sensitive cell array.

22. The method of claim 17, further comprising:
receiving a second medical tool through the first grasper;
receiving the second medical tool at a second grasper proximal end of a second grasper;
receiving the second medical tool through the second grasper past a second grasper distal end of the second grasper;
receiving the second medical tool through a third sensor coupled to the second grasper distal end;
identifying the second medical tool by the third sensor; and
grasping the second medical tool by the second grasper upon the third sensor identifying the second medical tool.

23. The method of claim 21, further comprising:
receiving the first medical tool through a second sensor coupled to the first grasper proximal end;

identifying the first medical tool by the second sensor before the first sensor identifies the first medical tool;

receiving the second medical tool through a fourth sensor coupled to the second grasper proximal end; and identifying the second medical tool by the fourth sensor before the third sensor identifies the second medical tool, wherein identifying the second medical tool by the fourth sensor comprises determining the diameter of the second medical tool and further wherein identifying the second medical tool by the third sensor comprises determining a diameter of the second medical tool;

determining whether the diameter from the third sensor is approximately equal to the diameter from the fourth sensor;

determining whether the diameter from the third sensor and the diameter from the fourth sensor are approximately equal to a predefined diameter of the second medical tool; and grasping by the second grasper the second medical tool upon determining the diameter from the third sensor and the diameter from the fourth sensor are approximately equal to the predefined diameter of the second medical tool.

24. The method of claim 23, wherein determining the diameter of the first medical tool comprises measuring a shadow cast by the first medical tool on a first light sensitive cell array and determining the diameter of the second medical tool comprises measuring a shadow cast by the second medical tool on a second light sensitive cell array.

25. A device for simulation of a medical procedure for using at least two of a first medical tool, a second medical tool, a third medical tool, or a fourth medical tool, comprising:

a first carriage, comprising:
   a first sensor configured to create a first output upon sensing a medical tool;
   a capture mechanism configured to create an aperture through the first carriage; and
   a second sensor configured to create a second output upon sensing a medical tool;
   wherein the capture mechanism of the first carriage is positioned between the first sensor and the second sensor;
a first motor configured to provide haptic effects to a user via the first carriage;
a first control circuit configured to:
   determine a medical tool passing through the first sensor and the second sensor from the first medical tool, the second medical tool, the third medical tool, and the fourth medical tool using the first output and second output of sensing the medical tool; and
   determine if the medical tool is to be grasped by the capture mechanism of the first carriage;
   wherein the capture mechanism of the first carriage is configured to grasp the medical tool upon the first control circuit determining that the medical tool is to be grasped;
a second carriage positioned at a distal end of the first carriage, comprising:
   a third sensor configured to create a third output upon sensing a medical tool;
   a capture mechanism configured to create an aperture through the second carriage; and
   a fourth sensor configured to create a fourth output upon sensing a medical tool;
   wherein the capture mechanism of the second carriage is positioned between the third sensor and the fourth sensor;
a second motor configured to provide haptic effects to the user via the second carriage;
a second control circuit configured to:
   determine a medical tool passing through the third sensor and the fourth sensor from the first medical tool, the second medical tool, the third medical tool, and the fourth medical tool using the third output and fourth output of sensing the medical tool if the second carriage is to be used in the medical procedure; and
   determine if the medical tool is to be grasped by the capture mechanism of the second carriage;
   wherein the capture mechanism of the second carriage is configured to grasp the medical tool upon the second control circuit determining that the medical tool is to be grasped;
a third carriage positioned at a distal end of the second carriage, comprising:
   a fifth sensor configured to create a fifth output upon sensing a medical tool;
   a capture mechanism configured to create an aperture through the third carriage; and
   a sixth sensor configured to create a sixth output upon sensing a medical tool;
   wherein the capture mechanism of the third carriage is positioned between the fifth sensor and the sixth sensor;
a third motor configured to provide haptic effects to the user via the third carriage;
a third control circuit configured to:
   determine a medical tool passing through the fifth sensor and the sixth sensor from the first medical tool, the second medical tool, the third medical tool, and the fourth medical tool using the fifth output and sixth output of sensing the medical tool if the third carriage is to be used in the medical procedure; and
   determine if the medical tool is to be grasped by the capture mechanism of the third carriage;
   wherein the capture mechanism of the third carriage is configured to grasp the medical tool upon the third control circuit determining that the medical tool is to be grasped;
a fourth carriage positioned at a distal end of the third carriage, comprising:
   a seventh sensor configured to create a seventh output upon sensing a medical tool;
   a capture mechanism configured to create an aperture through the fourth carriage; and
   a eighth sensor configured to create a eighth output upon sensing a medical tool;
   wherein the capture mechanism of the fourth carriage is positioned between the seventh sensor and the eighth sensor;
a fourth motor configured to provide haptic effects to the user via the fourth carriage;

a fourth control circuit configured to:
   determine a medical tool passing through the seventh sensor and the eighth sensor from the first medical tool, the second medical tool, the third medical tool, and the fourth medical tool using the seventh output and eighth output of sensing the medical tool; and
   determine if the medical tool is to be grasped by the capture mechanism of the fourth carriage;

wherein the capture mechanism of the fourth carriage is configured to grasp the medical tool upon the fourth control circuit determining that the medical tool is to be grasped.

* * * * *